US005509803A

United States Patent [19]
Gwilliam et al.

[11] Patent Number: 5,509,803
[45] Date of Patent: Apr. 23, 1996

[54] TOOLS FOR DENTAL WORK

[76] Inventors: Douglas G. Gwilliam, 31 Churchill Road, Gloucester, United Kingdom, GL1 5BS; David G. Norman, Plump Hillm, Mitcheldean, Gloucester, United Kingdom, GL17 OET

[21] Appl. No.: 204,233

[22] PCT Filed: Jul. 5, 1993

[86] PCT No.: PCT/GB93/01406

§ 371 Date: Mar. 4, 1994

§ 102(e) Date: Mar. 4, 1994

[87] PCT Pub. No.: WO94/01052

PCT Pub. Date: Jan. 20, 1994

[30] Foreign Application Priority Data

Jul. 4, 1992 [GB] United Kingdom ............... 9214280

[51] Int. Cl.⁶ ............................................. A61C 3/06
[52] U.S. Cl. .................................... 433/166; 51/298
[58] Field of Search ........................... 433/165, 166; 51/298, 293, 307, 309

[56] References Cited

U.S. PATENT DOCUMENTS

| | | | |
|---|---|---|---|
| 2,562,587 | 7/1951 | Swearington | 433/166 |
| 3,142,138 | 7/1964 | Kean et al. | 433/166 |
| 4,042,347 | 8/1977 | Sioui | 51/298 R |
| 5,273,559 | 12/1993 | Hammar et al. | 433/166 |

FOREIGN PATENT DOCUMENTS

| | | | |
|---|---|---|---|
| 2230195 | 12/1972 | Germany | 433/166 |
| 3314445 | 11/1983 | Germany | 433/166 |
| 6022983 | 2/1994 | Japan | 433/166 |

*Primary Examiner*—Cary E. O'Connor
*Attorney, Agent, or Firm*—Young & Thompson

[57] ABSTRACT

A dental tool for shaping teeth has a shank for fitting to a rotary drive and an abrasive head on the shank for working on teeth. For false teeth, the shank diameter, at least at the end that fits the drive, will be 2.35 mm, while for real teeth that diameter will be 1.6 mm. The head comprises diamond grit in a resin matrix, the resin preferably being a resole phenolic resin. Further particulate filler may be added.

10 Claims, 1 Drawing Sheet

TOOLS FOR DENTAL WORK

FIELD OF THE INVENTION

This invention relates to tools for dental work. It can be applied in one form to rotary tools used by dental technicians in shaping false teeth, and in another form to the drill bits used by dentists themselves.

BACKGROUND OF THE INVENTION

Currently, dental technicians mostly use two kinds of rotary tool, each of which are made in many different shapes and sizes to cope with the complex shapes of teeth. The number of tools deemed necessary make it complicated and expensive to practise in this field. But also, the tools do not last. One kind has heads which are miniature grindstones, abrasive stone or grit bonded with resin being moulded onto the end of a stainless steel shank. But they tend soon to wear smooth or clog up and they are prone to overheating. It appears that, in the field, no-one has used resin bonded diamond grit which is theoretically the best and most long lasting abrasive. When it has been used, it has generally been adhered by nickel plating to the surface of a stainless steel shank. The problem again is that once the grit is dislodged or worn the tool is useless, and it tends to clog and generate heat. Sintered diamond heads (the diamonds being metal bonded in a mould) have also been tried, but they also clog and overheat.

OBJECT OF THE INVENTION

It is the aim of this invention to provide a tool capable of much longer life and relative coolness in operation, and where just a few rather than dozens wall generally give a sufficient range.

SUMMARY OF THE INVENTION

According to the present invention there is provided a rotary tool for dental work comprising a shank carrying a head of diamond grit in a resin matrix, the shank having a diameter at the end opposite the head in accordance with the ISO standard for dental usage.

Currently, this standard specifies a diameter of 2.334–2.35 mm for dental tools used by technicians shaping false teeth. Their drive speed is usually in the range of 10,000 to 50,000 rpm. But a dentist, working on real teeth, has slightly smaller tools, and the standard currently specifies a diameter of 1.59 to 1.6 mm. The operating speed is of the order of 50,000 rpm.

It will generally be convenient to fix the abrasive head to a member of larger diameter than those quoted above, and so the portion that is engaged by the drive may be of reduced diameter compared with the end bearing the head. That end will preferably be knurled or otherwise roughened to afford a good grip for the resin, which serves also to bond the head to the shank.

The resin of the matrix is preferably a phenolic resin and in particular one in the resole group in which the formaldehyde to phenol ratio is greater than one, and usually in the range 1.2 to 3.5. A catalyst, in particular an acid, may be added to promote curing. To reduce the brittleness of such resin there may be other particulates besides the diamond grit, such as silicon carbide, aluminium oxide, silica flour, calcium oxide, graphite, molybdenum disulphide, PTFE, bronze, nickel and copper. Other additives may include silane, furfuraldehyde, phenolic resin adhesives and sulphur.

It is also envisaged that certain polyimide resins could be suitable.

The head can be moulded to various shapes. It can be used for grinding, shaping, characterising and profiling all the widely used dental materials including porcelain, enamel, non-precious metals, semi-precious metals, gold, crown and bridge acrylic, and ceramics. It is non-toxic, non-contaminating, non-clogging and stays cool in operation and sharp even though it does gradually wear away. Fresh diamond grit comes to the surface as the old is carried away with the surface layer of resin. Of course, this means that the head does gradually change shape, but that can be turned to advantage. The technician acquires a set of differently shaped and still efficient tools simply by using the basic original set, and so with steady replacement of the originals he can build up a large collection of considerable variety. In the same way, a dentist working on real teeth can acquire a comprehensive set from a relatively small selection.

BRIEF DESCRIPTION OF THE DRAWING

By way of example, the accompanying drawing shows a basic set of four tools in respectively numbered figures, in which.

DETAILED DESCRIPTION OF THE INVENTION

Figure 1:
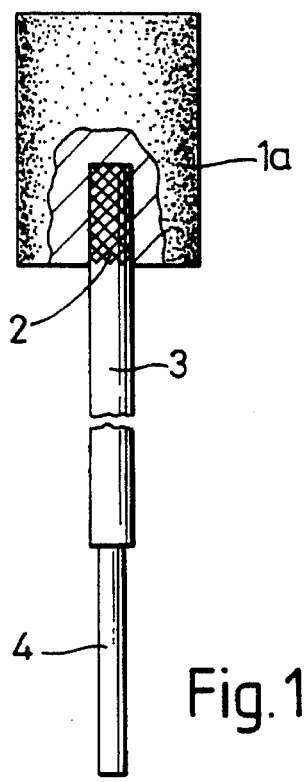
FIG. 1 is an elevational view, partly in cross section, of a dental tool according to the present invention.
Figure 2:
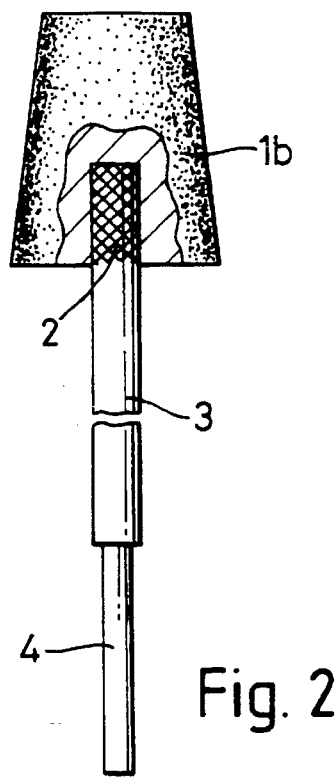
FIGS. 2–4 are views similar to FIG. 1 but showing modified embodiments thereof.
Figure 3:
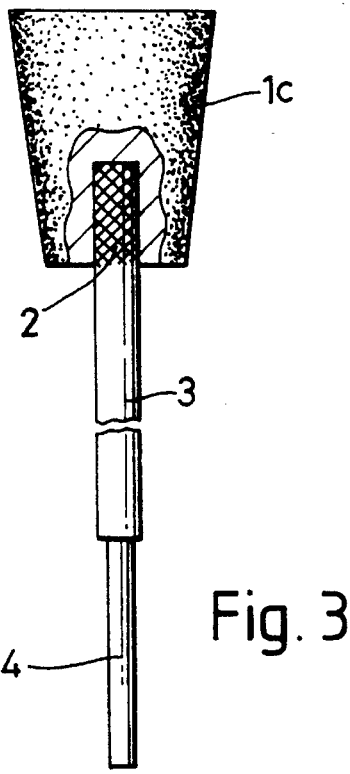
Figure 4:
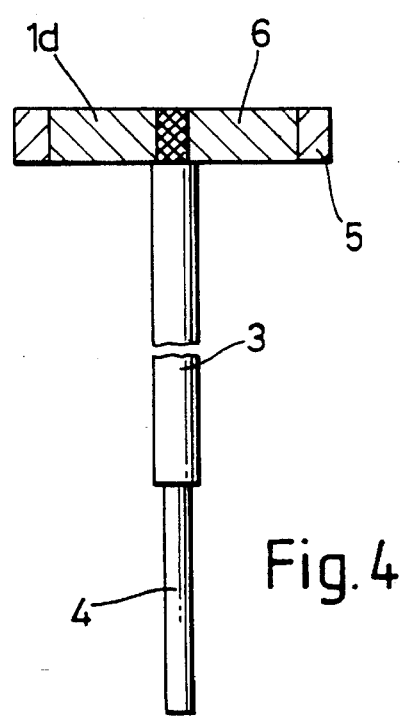

Each tool has a head of diamond grit in a resin matrix bonded by the resin to the knurled end 2 of a stainless steel shank 3. The other end 4 is of reduced diameter, either 2.35 mm or 1.5 mm, or at least within the bounds of the ISO standard referred to above. There is a cylindrical head 1a, two frusto-conical heads 1b and 1c, one reversed with respect to the other, and a disc-like head 1d. Typically for a dental technician the cylindrical head 1a might be 6 mm in diameter and 8 mm in length on a 40 mm length shaft. The frustoconical heads 1b and 1c might be of similar length and maximum diameter, both reducing to 4.5 mm at the smaller end.

The cylindrical and frusto-conical heads are of resin and diamond throughout, possibly with other filler material as referred to above, and are bonded to diamond knurling at the end of the shank. The head 1d of the disc tool is not wholly resin and diamond: this material is bonded in a thick annular band 5 to the periphery of a stainless steel disc 6 co-axially fitted to the end of the shank 3. The disc head 1d might be of the order of 22 mm in diameter with a thickness of 3 mm.

We claim:

1. A rotary tool for dental work comprising a shank carrying at one end a rigid head of diamond grit in a resin matrix and its other end being smoothly cylindrical and having a diameter in accordance with the ISO standard for dental usage, the head being moulded onto said one end to form an effectively unitary tool.

2. A rotary tool as claimed in claim 1, wherein said diameter is in the range 2.334–2.35 mm.

3. A rotary tool as claimed in claim 1, wherein said diameter is in the range 1.59–1.6 mm.

4. A rotary tool as claimed in claim 1, wherein said opposite end of the shank is of reduced diameter compared with the end bearing the head.

5. A rotary tool as claimed in claim 1, wherein the resin is a phenolic resin.

6. A rotary tool as claimed in claim 5, wherein the resin is a resole.

7. A rotary tool as claimed in claim 6, wherein the resole has a formaldehyde to phenol ratio in the range 1.2 to 3.5.

8. A rotary tool as claimed in claim 1, wherein the resin is a polyimide resin.

9. A rotary tool as claimed in claim 1, wherein other particulate material than diamond grit is embedded in the resin.

10. A rotary tool as claimed in claim 9, wherein the further particulate material is at least one of silicon carbide, aluminium oxide, silica flour, calcium oxide, graphite, molybdenum disulphide, PTFE, bronze, nickel and copper.

* * * * *